United States Patent
McNeely

(10) Patent No.: US 12,311,369 B2
(45) Date of Patent: May 27, 2025

(54) AUTOMATIC PLASMA SEPARATION AND METERING

(71) Applicant: GattaCo Inc., Murrieta, CA (US)

(72) Inventor: Michael Ryan McNeely, Murrieta, CA (US)

(73) Assignee: GattaCo Inc., Murrieta, CA (US)

( * ) Notice: Subject to any disclaimer, the term of this patent is extended or adjusted under 35 U.S.C. 154(b) by 0 days.

(21) Appl. No.: 18/211,778

(22) Filed: Jun. 20, 2023

(65) Prior Publication Data

US 2024/0024872 A1 Jan. 25, 2024

Related U.S. Application Data

(63) Continuation of application No. 17/163,711, filed on Feb. 1, 2021, now Pat. No. 11,717,827, which is a (Continued)

(51) Int. Cl.
*B01D 61/14* (2006.01)
*A61M 1/36* (2006.01)
(Continued)

(52) U.S. Cl.
CPC ......... *B01L 3/502753* (2013.01); *A61M 1/36* (2013.01); *B01D 61/14* (2013.01);
(Continued)

(58) Field of Classification Search
CPC ............. B01L 3/502753; B01L 3/5023; B01L 2200/026; B01L 2200/0605; B01L 2200/16; B01L 2300/0681; B01L 2300/069; B01L 2300/0861; B01L 2400/0406; B01L 2400/0457; G01N 33/491; A61M 1/36; A61M 2205/33; B01D 61/14; B01D 63/087
See application file for complete search history.

(56) References Cited

U.S. PATENT DOCUMENTS 10,532,325 B2  1/2020  Mcneely
10,906,042 B2  2/2021  McNeely et al.
(Continued)

FOREIGN PATENT DOCUMENTS

WO  WO-2012015926 A2  2/2012
WO  WO-2015044454 A2  4/2015
(Continued)

OTHER PUBLICATIONS

"U.S. Appl. No. 15/745,707, Examiner Interview Summary mailed Apr. 7, 2020", 4 pgs.
(Continued)

*Primary Examiner* — John Kim
(74) *Attorney, Agent, or Firm* — Schwegman Lundberg & Woessner, P.A.

(57) ABSTRACT

A new method is disclosed for extracting plasma from whose blood and metering the amount of plasma to an exact volume for dispensing into a diagnostic test, in a fully automatic and self-contained device. The device can be used in resource limited settings by unskilled users to facilitate sophisticated medical diagnostic testing outside of a hospital, clinic or laboratory.

20 Claims, 9 Drawing Sheets

Related U.S. Application Data continuation of application No. 15/745,707, filed as application No. PCT/US2016/042865 on Jul. 18, 2016, now Pat. No. 10,906,042.

(60) Provisional application No. 62/249,922, filed on Nov. 2, 2015, provisional application No. 62/195,281, filed on Jul. 21, 2015.

(51) Int. Cl.
*B01D 63/08* (2006.01)
*B01L 3/00* (2006.01)
*G01N 33/49* (2006.01)

(52) U.S. Cl.
CPC .......... *B01D 63/087* (2013.01); *B01L 3/5023* (2013.01); *G01N 33/491* (2013.01); *A61M 2205/33* (2013.01); *B01L 2200/026* (2013.01); *B01L 2200/0605* (2013.01); *B01L 2200/16* (2013.01); *B01L 2300/0681* (2013.01); *B01L 2300/069* (2013.01); *B01L 2300/0861* (2013.01); *B01L 2400/0406* (2013.01); *B01L 2400/0457* (2013.01)

(56) References Cited

U.S. PATENT DOCUMENTS

| | | |
|---|---|---|
| 2006/0011545 A1 | 1/2006 | Latza |
| 2013/0175213 A1 | 7/2013 | Dorrer et al. |
| 2018/0207638 A1 | 7/2018 | Mcneely |
| 2021/0146360 A1 | 5/2021 | Mcneely |

FOREIGN PATENT DOCUMENTS

| | | |
|---|---|---|
| WO | WO 2015/134809 A1 * | 9/2015 |
| WO | WO-2015191406 A1 | 12/2015 |
| WO | WO-2017015243 A1 | 1/2017 |

OTHER PUBLICATIONS

"U.S. Appl. No. 15/745,707, Final Office Action mailed Jul. 6, 2020", 7 pgs.
"U.S. Appl. No. 15/745,707, Non Final Office Action mailed Jan. 2, 2020", 17 pgs.
"U.S. Appl. No. 15/745,707, Notice of Allowance mailed Sep. 23, 2020", 7 pgs.
"U.S. Appl. No. 15/745,707, Response filed May 4, 2020 to Non Final Office Action mailed Jan. 2, 2020", 11 pgs.
"U.S. Appl. No. 15/745,707, Response filed Sep. 8, 2020 to Final Office Action mailed Jul. 6, 2020", 8 pgs.
"U.S. Appl. No. 17/163,711, Non Final Office Action mailed Dec. 6, 2022", 6 pgs.
"U.S. Appl. No. 17/163,711, Notice of Allowance mailed Mar. 23, 2023", 7 pgs.
"U.S. Appl. No. 17/163,711, Response filed Mar. 6, 2023 to Non Final Office Action mailed Dec. 6, 2022", 7 pgs.
"International Application Serial No. PCT/US2016/042865, International Preliminary Report on Patentability mailed Feb. 1, 2018", 8 pgs.
"International Application Serial No. PCT/US2016/042865, International Search Report mailed Oct. 4, 2016", 2 pgs.
"International Application Serial No. PCT/US2016/042865, Written Opinion mailed Oct. 4, 2016", 6 pgs.

* cited by examiner

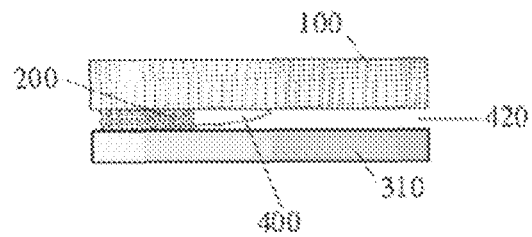
*FIG. 1*
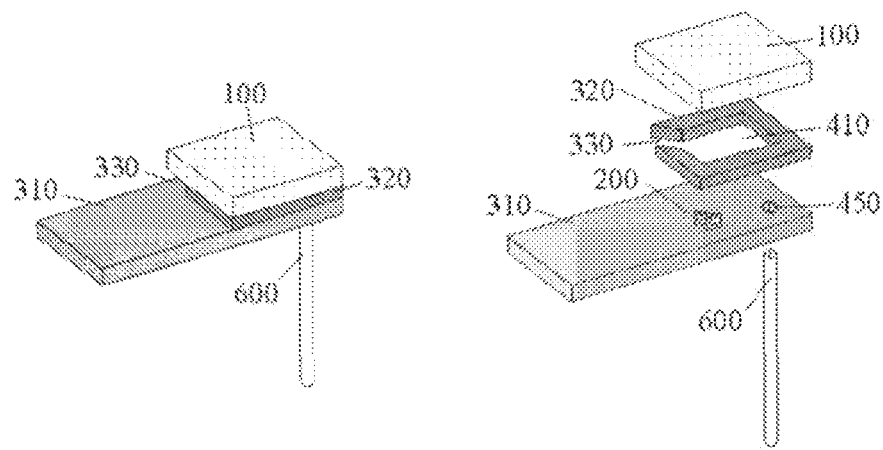
(a)           (b)
*FIG. 2a & b*

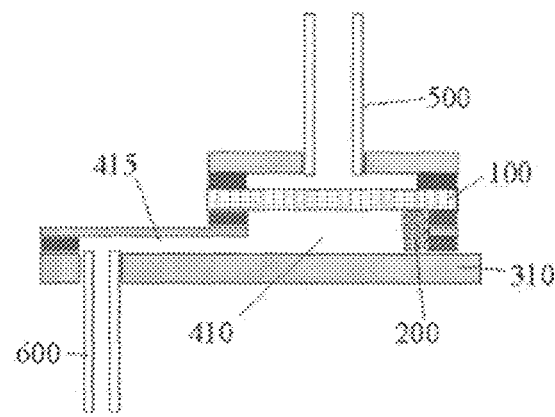
*FIG. 11*
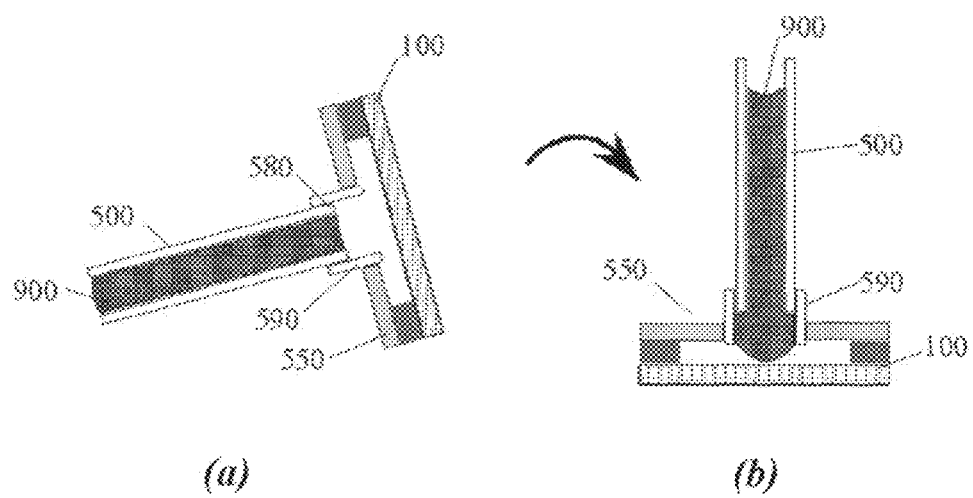
*FIG. 12a & b*

AUTOMATIC PLASMA SEPARATION AND METERING

CROSS-REFERENCE TO RELATED APPLICATION

This application claims priority to and the benefit of U.S. application Ser. No. 17/163,711, filed on Feb. 1, 2021, now U.S. Pat. No. 11,717,827, which claims priority to and the benefit of U.S. application Ser. No. 15/745,707, filed on Jan. 18, 2018, now U.S. Pat. No. 10,906,042, which is a national-stage application filed under 35 U.S.C. 371 of PCT Application No. PCT/US2016/042865, filed on Jul. 18, 2016, which claims priority to and the benefit of U.S. provisional application No. 62/195,281, filed on Jul. 21, 2015 and U.S. provisional application No. 62/249,922, filed on Nov. 2, 2015, which are incorporated herein by reference.

BACKGROUND OF THE INVENTION

Field of the Invention: This invention discloses a method of extracting plasma from whole blood in an automatic fashion using a plasma separation membrane, capillary forces, and a novel capillary reset valve or mechanism (CPR-Valve). The CPR-Valve automatically overcomes the breakthrough pressure of the plasma separation membrane allowing the plasma extraction, collection and metering processes all to take place without any external forces, energy or action on the part of the user or need of additional support equipment.

Description of Related Art: Many attempts have been made at separating plasma from whole blood in a stand-alone device, as a means of replacing the common method of centrifugation. Plasma is often required for the detection of blood-based biomarkers because, in many cases, the cellular components of blood interfere with detection of these biomarkers. Centrifugation, however, is a fairly complex task involving skilled personnel, complex, heavy and large equipment, and electrical power. In addition, a means for obtaining the whole blood is needed, which is usually performed by a venous puncture and blood draw by another skilled person, namely a phlebotomist. Finally, another or one of the same skilled workers is needed for performing the centrifugation, measuring the required volume of plasma, and dispensing the plasma into the diagnostic device, usually using a pipette. In automated systems some of these manual steps can be replaced with robotic processes of loading, spinning, measuring and dispensing. However, these automated systems are usually even more complex, expensive, large and sophisticated than a simple centrifuge. The need for replacing all of these steps in a simple, affordable, and easy to use device is the focus of numerous, as yet commercially unsuccessful, efforts.

Many attempts at replacing the centrifuge use commercially available Plasma Separation Membranes (PSM), such as the Pall Vivid™ PSM or International Point of Care Primecare PSM. Numerous scientific articles have been published describing devices comprised of these membranes, as well as support structures required for adding the whole blood, collecting the separated plasma and, in all cases, some means of overcoming the breakthrough pressure of the PSM to allow the plasma to pass through the membrane and be collected.

Many of these articles detail the biochemical nature of the plasma that is collected and compare it to plasma derived from centrifugation. Most comparisons are favorable, which should lead to rapid adoption of these processes due to the commercial need of such technology. However, it has not, and there is, to date, no readily available and commonly used centrifuge replacement device. This is most likely due to the complex method of sample handling, collection, difficult, complex, or expensive method of overcoming the breakthrough pressure of the PSM, and related issues that lead to designs that are not commercially viable, ether due to cost, complexity of use, or poor performance.

BRIEF SUMMARY OF THE INVENTION

The disclosed technology details a new method of overcoming the breakthrough pressure of hydrophilic membranes, in this case the Plasma Separation Membrane (PSM), and the design advantages made possible by this new method. These design advantages include the ability to design exactly where the plasma breaks through, how the flow of plasma through the membrane proceeds, where it stops, and how all parameters can be easily controlled using passive capillary forces, leading to a completely automatic, self-contained, disposable device that is easily used and inexpensive to manufacture.

A device for overcoming the breakthrough pressure of the PSM makes use of a new mechanism described as a Capillary Pressure Reset (CPR) Valve or mechanism. This valve is comprised of a soluble matrix that has a high enough capillarity to draw liquid through a hydrophilic membrane or filter (e.g., the PSM) under passive capillary forces, thereby eliminating the membrane's inherent breakthrough pressure, and then dissolving in the extracted liquid (the plasma) and releasing the liquid into a new geometry that has lower capillarity.

By placing the soluble matrix comprising the CPR-Valve in a strategic location at one end of a plasma pooling or collection channel, the initial breakthrough point and direction of flow of the plasma can be design to proceed in a repeatable manner. This flow or filling process can be designed to ensure no bubbles are trapped, which can lead to accurate, repeatable filling of a precise geometry of known volume, leading to the plasma being metered to a known volume prior to dispensing.

Several examples of how the technology is used, and specific details of the design parameters of complete systems, are disclosed.

BRIEF DESCRIPTION OF THE SEVERAL VIEWS OF THE DRAWINGS

The following drawings illustrate exemplary embodiments for carrying out the invention. There are, in fact, many possible configurations, housings, flow systems, entrance and exit point designs, flow patterns, Capillary Pressure Reset (CPR)-Valve placements, dimensions and geometries including rectangular or cylindrical flow channels, and liquid flow driving forces possible in various embodiments of the invention. The following examples only serve to illustrate principles discussed in this disclosure, and are not meant to be limiting in any way in converting the principles discussed in this disclosure into physical form, and are not necessarily to scale as may be used in a physical system. Like reference numerals refer to like parts in different views or embodiments of the present invention in the drawings.

FIG. 1 illustrates the basic concept of CPR-Valve placement in contact with the bottom surface of a Plasma Separation Membrane (PSM), and the flow of plasma to fill a space under the PSM.

FIGS. 2a and b illustrates assembled (a) and exploded (b) views of a structure useful for separating plasma from a whole blood sample and delivering a metered volume of that plasma into a capillary tube inserted into the plasma pooling area according to an embodiment of the invention.

FIG. 11 illustrates a profile view of a multi-layered laminate design showing an extension of the plasma pooling area useful for improving the efficiency of a device according to an embodiment of the invention.

FIGS. 12a and 12b illustrate the use of a capillary stop junction near the outlet of the input capillary to ensure precise volume control of the input whole blood added to the PSM according to an embodiment of the invention.

DETAILED DESCRIPTION OF THE INVENTION

Figure 3:
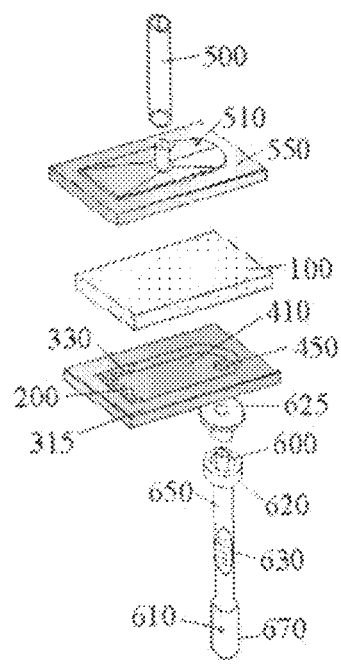
FIG. 3 illustrates a layer by layer view of a thermoformed or injection-molded structure useful for separating plasma from a whole blood sample introduced into a metering input capillary and the plasma collected into a specially modified capillary tube designed to also function as a removable pipetting device according to an embodiment of the invention.

Certain embodiments as disclosed herein provide for an automatic plasma separation device. After reading this description it will become apparent to one skilled in the art how to implement the invention in various alternative embodiments and alternative applications. Although various embodiments of the present invention will be described herein, it is understood that these embodiments are presented by way of example only, and not limitation. As such, this detailed description of various alternative embodiments should not be construed to limit the scope or breadth of the present invention.

Capillary Pressure Reset (CPR)-Valve: The breakthrough pressure of a membrane is defined as the pressure required to force liquid (filtrate) through the downstream surface of a membrane. In simplified form the breakthrough pressure can be considered as multiple capillary stop junctions as the pores on the bottom surface of the membrane open to the space below the membrane. The breakthrough pressure is dependent on the membrane material composition, pore size and liquid filtrate properties. In the disclosed design the soluble matrix of which the CPR-Valve is comprised is in physical contact with the bottom surface of the Plasma Separation Membrane (PSM) and represents a zone of higher capillarity than the PSM itself. The CPR-Valve material is usually comprised of a simple sugar, but can take many forms depending on the needs of the system. The placement of the CPR-Valve in physical contact with the bottom surface of the PSM causes the liquid (plasma) within the PSM to flow into the CPR-Valve under capillary action. Once plasma is within the CPR-Valve, the soluble material dissolves, releasing the plasma as a free-standing drop into the space between the PSM and the base of the plasma pooling area. In this fashion, no external pressure is applied in order for the PSM's inherent breakthrough pressure to be overcome. The droplet of plasma forms a connection or meniscus between the bottom surface of the PSM and the base of the pooling area. The presence of plasma within this space and in contact with the bottom surface of the PSM allows the plasma to continue to flow through the bottom surface of the PSM as it wicks along the space, with the meniscus being drawn forward due to capillary action, eliminating the capillary barriers retaining additional plasma within the small bottom pores of the PSM. This contributes to additional flow of plasma into the pooling area and causes the meniscus to spread further. The capillary force caused by the meniscus bound by the hydrophilic surfaces of the bottom surface of the PSM and base material continues to draw meniscus forward, breaking additional capillary barriers as it spreads. In this manner the entire surface area of the PSM can be recruited to separate plasma, not just in the area of the placement of the CPR-Valve.

FIG. 1 illustrates a typical geometry profile of the PSM 100, CPR-Valve 200 and base material 310. The spread or movement of the meniscus 400 formed between the PSM and base material leading to a point 420 where the separated plasma may be collected. FIG. 2 illustrates how a capillary tube 600 can be introduced into the plasma pooling space 410 through a hole 450 in the bottom of the base material 310. Plasma will flow into the capillary by capillary force provided the physical and material parameters of the capillary tube satisfy the conditions of continued capillary flow, to be discussed more later in this disclosure.

Flow through the PSM will continue until all plasma available for collection has passed through, until the pores of the PSM become blocked by cellular components of the whole blood or until the lagging end of flow generates a higher capillary barrier than is present at the leading end of flow. However, if flow does not continue through the PSM, it is still possible to collect, or extract, all plasma that has pooled under the PSM. This is possible by placing a venting duct 330 in the system, FIG. 2, which allows air to pass into the plasma pooling space 410 as plasma is drawn out of the same space and into the capillary tube 600. The vent 330 acts as a capillary barrier and does not allow plasma to exit the plasma pooling area 410 under normal operating conditions.

Lack of venting would generate a vacuum back pressure, which would prevent any additional plasma from being collected, except what may be pulled through the PSM by the capillary forces of the capillary itself, in excess of the volume of the plasma pooling area.

The strategic placement of the vent 330 will also allow the region under the PSM, where the original CPR-Valve 200 was located, to be bypassed while plasma is being collected from the plasma pooling area 410. This causes all, or the majority, of dissolved soluble matrix of which the CPR-Valve is comprised, to remain in the plasma pooling area and not be passed into the capillary tube 600.

By strategic placement of the CPR-Valve, vent, and capillary output, a system can be produced that reliably and repeatedly allows for plasma to be extracted from whole blood, fill a pre-defined space or channel, defined by the geometry of the space walls 320, top 100 and base 310, without trapping bubbles, and deliver the extracted plasma into a capillary tube 600, which can be removed and used to dispense the collected plasma anywhere it is needed.

Capillary Pipette: The physical and material parameters that are needed for plasma to enter the inserted capillary tube under passive capillary forces are defined by the capillary force equation shown here:

$$P = -\frac{2\sigma \cos \theta}{r} \quad (1)$$

where: P Capillary Pressure
r radius of pore or flow channel
θ contact angle of channel or membrane material
σ surface tension of liquid A negative pressure is similar to a suction force that draws liquid into the system. A contact angle greater than 90° represents a hydrophobic material, and the resulting capillary pressure turns positive, indicating a positive force is required to push liquid into the system.

At the point where the capillary tube enters the plasma pooling area, an interface exists between two different geometries. In order for plasma to flow into the capillary tube, the capillary pressure, or capillarity, of the geometry and material of the capillary tube must be greater than the capillarity of the geometry and materials comprising the plasma pooling area. In other words, the difference between $P_{cap}$ (or just $P_c$) and $P_{pool}$ (or just $P_p$) must remain negative, as is illustrated by this equation:

$$\Delta P = P_c(\sigma_c, \theta_c, r_c) - P_p(\sigma_p, \theta_p, r_p) = \frac{2\sigma_p \cos \theta_p}{r_p} - \frac{2\sigma_c \cos \theta_c}{r_c} \quad (2)$$

The surface tension (σ) between the liquid (plasma) and air does not change from one geometry to the next, so $\sigma_c = \sigma_p$, which allows the equation to be simplified to:

$$\Delta P/2\sigma = \frac{\cos \theta_p}{r_p} - \frac{\cos \theta_c}{r_c} \quad (3)$$

The geometry of the flow channel in the capillary tube is cylindrical, with a known radius $r_c$, but the geometry of the pooling area is rectangular, requiring an effective hydraulic radius to be calculated, based on the equation:

$$r_p = \frac{ab}{a+b} \quad (4)$$

where: $r_p$ Effective hydraulic radius of the pooling area
a height of pooling area flow channel
b width of pooling area flow channel For example, in a case, such as where the height of the pooling area flow channel is 170 µm, and the width is 1250 µm, the effective radius can be calculated to be approximately 150 µm. In the case where the capillary tube also has a radius of approximately 150 µm, equation (3) can be simplified to:

$$\Delta Pr/2\sigma = \cos \theta_p - \cos \theta_c \quad (5)$$

If the material of the pooling area is mainly derived of hydrophilic plastics, which may have a contact angle ($\theta_p$) of around 75°, and the capillary tube is comprised of glass, with a contact angle ($\theta_c$) of around 15°, cos(75°)=0.26 and cos(15°)=0.97, the difference is negative, allowing flow to continue into the capillary tube.

In the case where the radii of the two geometries are not approximately the same, and it is desired to derive an equation that clarifies what the relationship between $r_c$ and $r_p$ should be, in order for the capillary pressure at the junction to remain negative, the following relationship can be derived from equation (3), namely:

$$r_p \cos \theta_c > r_c \cos \theta_p \quad (6)$$

Using the same contact angles as before, and rearranging to emphasize the desired radius of the capillary tube, we obtain:

$$r_c < 3.7 r_p \quad (7)$$

While this relationship is useful to keep in mind, it does not take into account some very critical issues associated with microfluidics, capillary forces, and commercially viable manufacturing and assembly issues in general. These issues include variability in material properties, surface roughness, and in particular, precise alignment between surfaces and junctions.

Considering the illustration shown in FIG. 3, an input metering capillary 500 is used to deliver a minimum volume of whole blood to the PSM 100. A cover 550 is also used to facilitate wicking of the blood across the whole PSM, rather than just pooling nearest to the input capillary. The alignment between the input capillary 500, the cover 550, and PSM 100 is important to ensure blood reaches the PSM and can be distributed. The blood in the capillary will also be subject to gravity, in addition to capillary forces, such that, if the capillary tube does not fully reach the PSM, the blood in the capillary tube may extend slightly past the end of the capillary tube to aid in bridging any gap.

However, if the capillary tube extends too far past the bottom surface of the cover, it may become imbedded into the PSM, preventing proper wetting of the PSM and adequate pooling of blood across the whole surface area of the PSM to facilitate even plasma extraction.

Figure 4:
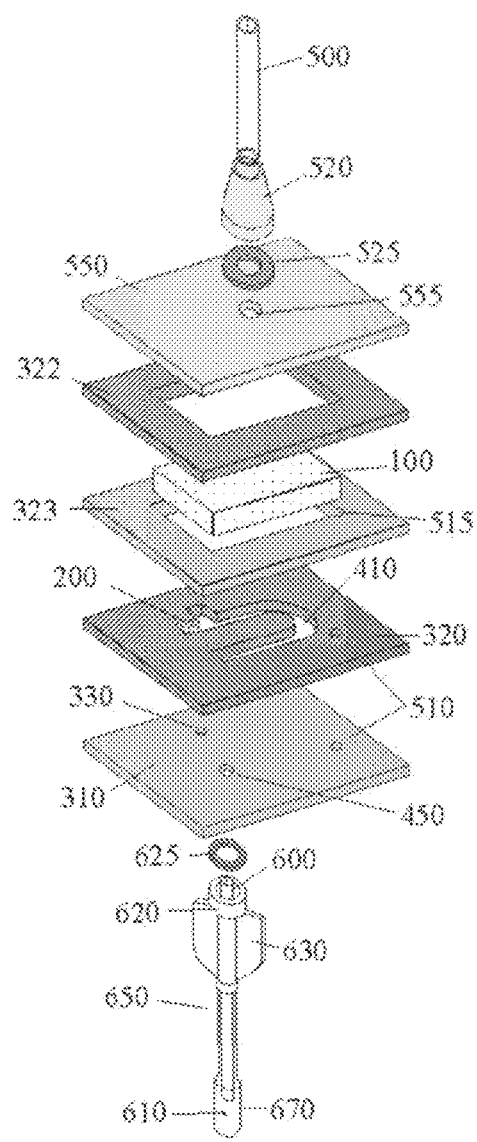
FIG. 4 illustrates a similar design as FIG. 3, except that this design is comprised of laminated layers rather than injection molded or thermoformed parts according to an embodiment of the invention.

Also to facilitate even distribution of the input blood sample, an input vent 510 is needed. As blood covers the PSM, air in the space between the PSM and the cover and air within the PSM must be vented out. This may take place by air passing through the plasma pooling area 410 and out through the output capillary pipette 650, but it is more reliable to have a separate vent 510, either in the cover, as is illustrated in FIG. 3, or in the base, as is illustrated in FIG. 4. In either case, it is useful for the vent to be placed in a position where blood or plasma does not leak out during normal device operation. Also, as is illustrated in FIG. 4 and again in FIG. 7, it may be useful for the vent to be offset slightly from the location of the PSM 100 by placing a slot or notch 515 in the spacer surrounding the PSM 322 and 323 so that air may vent out all around the PSM and not be obstructed in any fashion by the input whole blood that covers the PSM.

To operate the device, the input capillary tube 500 should be slightly inclined with the body of the separation device slightly higher than the tip of the input capillary tube. The input is touched to a drop of blood that has formed on the surface of a finger previously punctured with a lancet or needle. The capillary tube should continue to draw blood into it until it reaches the end of the tube, which can be visually observed, or until it reaches the PSM itself, which is also visibly observable. At this time the device should be held upright to facilitate wicking of the blood across the whole upper surface of the PSM. Not all blood may leave the input capillary tube initially, but may slowly move down as the PSM saturates and plasma is extracted through the membrane.

If the input capillary tube is declined during filling, the blood in the tube may prematurely separate from the droplet on the finger and flow, by gravity, down the capillary tube. Attempting to add more blood may trap a bubble, preventing further flow.

As the plasma collects in the pooling area 410, it will spread and move toward an opening 450 which is the entrance of a capillary pipette 650 that is inserted through the base of the device. Rather than just a capillary tube, the capillary pipette 650 is illustrated in FIGS. 3-4 and 6-8, which is a capillary tube 600 modified with a plastic sheath for protection with finger gripping points 630, a squeeze bulb 670, a vent in the squeeze bulb 610, and a fitting 620 and 625 that allows for easy removal of the capillary pipette for dispensing the collected plasma where it is needed. The capillary tube can be made of glass, plastic, metal or other material that is hydrophilic or can be rendered suitably hydrophilic for the purpose of drawing plasma in by passive capillary forces. The upper surface of the capillary 600 within the capillary pipette 650 should be flush with the entrance of the hole or via 450 in the plasma pooling areas 410.

Although some metering of the plasma volume takes place due to the geometry of the pooling area, the exact volume of plasma collected into the capillary pipette can be precisely controlled by the geometry of the internal capillary 600 itself. Plasma enters this tube within the capillary pipette and is held by capillary stop junctions at its inlet and outlet. Air is vented out of the capillary through the small hole 610 in the pipette's squeeze bulb 670. The pipette can be removed from the body of the device using the finger grips 630, not by holding on to the squeeze bulb, and gently twisting the pipette while pulling it away from the body of the device. Once separated, the pipette can be moved around gently without fear of plasma exiting or dripping from it.

To dispense, the tip of the pipette is placed at the desired location of dispensing, the bulb is squeezed, with the vent hole 610 covered, and the plasma is then forced out of the internal capillary 600.

FIG. 3 illustrates a single, straight channel for the plasma pooling area 410, and a friction fitting for the capillary pipette 620 and 625. The body of the plasma extraction device is either thermoformed or injection molded and sealed or pinched round the edges including the edge of the PSM 100. FIG. 4 illustrates a laminated version of the plasma extraction device, with the plasma pooling area or channel 410 formed in an adhesive layer 320 in the shape of a 'U'. The capillary pipette 650 is held in place with a thin adhesive layer 625, and has more pronounced finger grips 630 to facilitate removal. A screw-type, or Luer fitting 620 can also be used to attach the capillary pipette to the body of the device, in addition to friction or adhesive. Instead of pinching or compressing the PSM 100 between the cover and base material as shown in FIG. 3, in FIG. 4 the PSM 100 is held within a cut-out section of a spacer comprised of plastic 323 and adhesive 322 layers, and rests on the adhesive layer 320 that forms the channels of the plasma collection area.

In FIGS. 3 and 4 the internal alignment between the plasma pooling area 410 and output capillary pipette 650 is critical to proper device function. This alignment can easily be achieved using standard device design and assembly methods. These include using robust, precision Luer lock fittings, or thin adhesive layers, with proper quality controls in place.

Another important element in device usage is to ensure plasma extraction and filling of the capillary pipette is complete before removal of the capillary pipette. This can be done by placing a contrasting agent or mark near the end of the capillary pipette that generates a visible difference between filled and unfilled capillaries. This could be a very thin and readily soluble inert dye placed within the capillary itself. During manufacturing of the device the dye could be inserted a short distance at the distal end of the capillary and then blown out once it has partially dried so that it does not clog or block flow of plasma filling the pipette, but leaves a light colored film that disappears once plasma has filled the capillary. Another method may be to scratch the inside of the distal end of the capillary with a diamond-tip bit, or similar device. The scratch marks would disappear when the capillary is filled with plasma. Alternatively, the inside surface of the distal end of the capillary could be coated with a hydrophobic film so that it is not filled. The difference between a filled and unfilled portion of the capillary, when they are side by side, can be recognized. Finally, if the capillary is held vertically, a very small volume of plasma may extend past the end of the capillary, showing that it is filled.

Direct Dispensing: In a previous example, the radius of the capillary was suggested to be 150 µm. If the desired volume the capillary pipette is to collect and dispense is 5 µL of plasma, then its required length can be easily determined by the relationship between volume and length of a cylinder with a known radius, as illustrated by the equation:

$$\text{Length}_c = \frac{Vol}{\pi r_c^2} \tag{8}$$

where: $r_c$ Radius of the capillary
Vol Desired capillary collection volume
For the case cited, Vol=5 µL, $r_c$=150 µm, then $\text{Length}_c$=70.8 mm, or 2.8 inches. In the design illustrated in FIG. 4, this $\text{Length}_c$ represents the length of the capillary 600 inside narrow diameter portion of the capillary pipette 650. The capillary can extend into the bulb region, but the minimum length of the entire capillary pipette will need to be at least 70.8 mm. Such a long length of an unsupported glass member begins to introduce fragility into the device design.

Consider further a case when a capillary tube of the same radius is used, but the desired collection volume is 10 µL rather than 5 µL. This requires a capillary of double the previous length, or 141 mm. It is possible the radius of the capillary tube can be increased to allow for a shorter capillary, using equation (8), in order to maintain a maximum capillary length of 70.8 mm, $r_c$ will need to be 212 µm to accommodate a volume of 10 µL. Fortunately this still satisfies the condition described by equation (7), using the same materials and geometry as used previously, with an effective $r_p$ of 150 µm. However, this requires the alignment of the output capillary to be much more precise in order to ensure reliable operation, which may be beyond the manufacturing constraints that allow a cost effective device to be produced.

Figure 5:
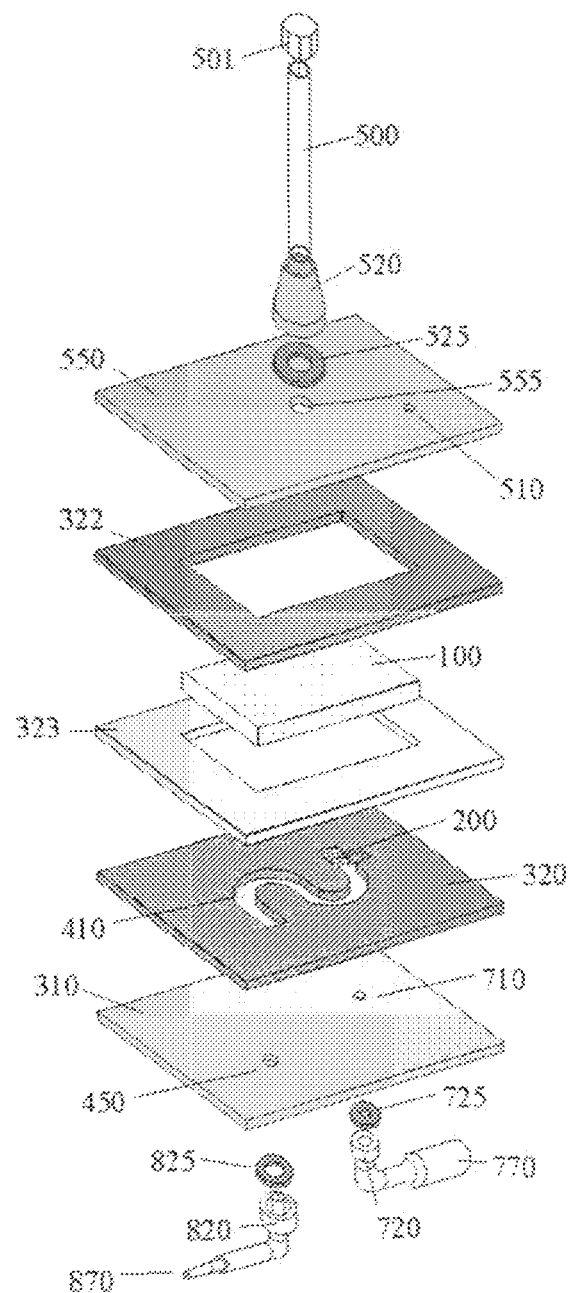
FIG. 5 illustrates another laminated plasma extraction and metering device where the metered plasma is dispensed directly from the body of the device, rather than collected into a removable capillary pipette according to an embodiment of the invention.

An alternative solution to the very long capillary tube or high precision manufacturing and assembly needs, is illustrated in FIG. 5. In this design the collected plasma is dispensed directly from the body of the device, rather than collected and dispensed from a removable capillary pipette.

The alignment challenges are much more relaxed because it is not intended for plasma to enter the squeeze bulb 770 or dispensing tip 870 regions under capillary forces because the interface to these regions are designed to represent capillary barriers which are not pushed past during plasma filling of the pooling or collection channel 410. Rather, positive pressure is applied by squeezing the bulb 770 to dispense plasma out of the pooling area, through the tip 870 and into an external receiving area.

An input capillary cover or cap 501 is needed to ensure any remaining whole blood is not ejected out through the input capillary 500 when the squeeze bulb is actuated. The suspended or unsupported area of the PSM 100, directly above the pooling area, may act as a type of movable diaphragm when the squeeze bulb is actuated. Care is needed to prevent this movement from causing leakage or ejection through the input capillary 500. The cap 501 would be put in place after the plasma has filled the plasma pooling area and before the squeeze bulb is actuated.

Figure 6:
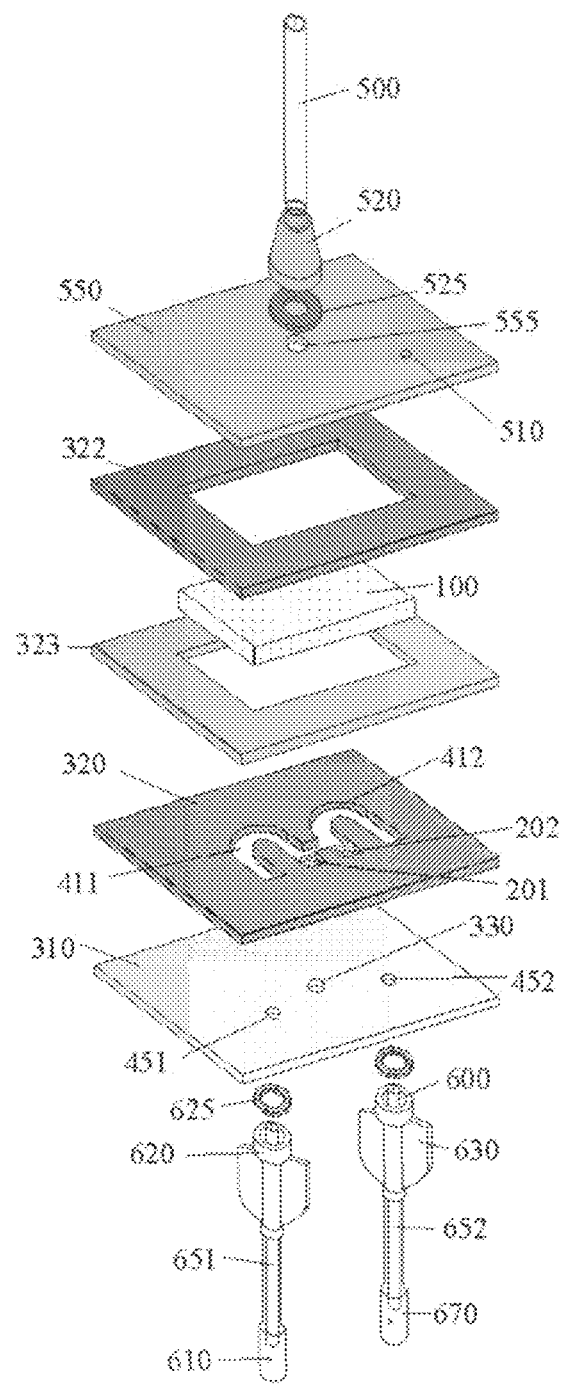
FIG. 6 illustrates an alternative geometry of a plasma extraction and metering device where the separated plasma is collected into two removable capillary pipettes useful for aliquoting the whole blood input into two separate plasma outputs for dispensing into two different diagnostic assays according to an embodiment of the invention.

Aliquot Plasma: FIG. 6 illustrates a design where a single input volume can be aliquoted into two output volumes. This provides another alternative to preventing excessively long output capillary pipettes, which can be accomplished by splitting the output into two different capillary pipettes 651 and 652, of either equal or unequal volumes. However, the primary advantage of this design is to enable dispensing two plasma volumes into two different destinations, but with only a single input requirement.

This method requires the two pooling areas 411 and 412 to be distinct from each other, including two separate CPR-valves 201 and 202. However, they may share a common vent 330 because the plasma does not connect or span across the vent in the design illustrated. Sharing a single channel (without a vent separating the two aliquots) and/or sharing a single CPR-valve leads to irregular and non-repeatable behavior, and does not ensure the two aliquots are divided repeatedly and reliably into the desired volumes.

Plasma Flow Within the PSM: Many of the membranes developed for plasma separation were initially developed for lateral flow applications, such as in lateral flow immunoassays. Hence, the separated plasma can actually flow quite well within the lateral dimensions of the PSM. Referring to FIG. 4, it has been observed on numerous occasions that the output capillary pipette 650 is able to completely fill before any air enters into the plasma pooling channel 410 through the vent 330. This can only be explained by plasma flowing laterally from any point on the PSM 100 and emptying into the channel 410 which feeds into the output capillary 600, rather than the pooling channel filling once and emptying once into the capillary.

This means that, at least in some cases, the plasma pooling channel 410 under the PSM is not effective in metering the volume of plasma passed downstream. Fortunately, the output is effectively metered by the output capillary 600. However, if the plasma pooling channel is not useful for metering, it can be eliminated or modified to serve other useful functions. Three modifications that can be made include 1) eliminating the output venting duct to simplify manufacturing; 2) making the pooling channel shorter to facilitate plasma reaching the output capillary more quickly; and, 3) making the adhesive layer thicker to allow for a larger diameter output capillary to be used while still retaining sufficient capillary forces needed to draw plasma into the output capillary.

Regarding a thicker adhesive layer, or greater distance between the bottom surface of the PSM and top surface of the base of the device, if this distance is too large it can become difficult for the meniscus to form between these two surfaces. However, assuming a meniscus does form, the larger space also makes the meniscus move more slowly forward. This is the reason the pooling channel can be shortened, so the more slowly advancing meniscus still reaches the output capillary within a reasonably short period of time.

If the space between the two surfaces is greater, the effective hydraulic radius discussed above with respect to equations (4)-(7) will be larger, which means the allowable radius of the output capillary can be larger, meaning its length shortened for the same metered volume.

Figure 7:
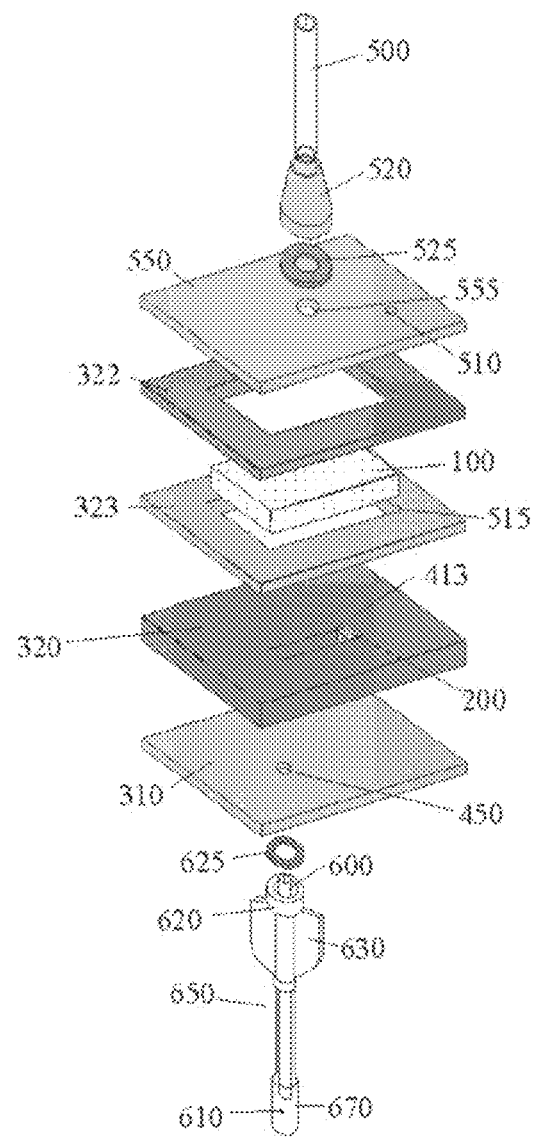
FIG. 7 illustrates a multi-layered laminate design with a short and deep plasma collection channel and no vent. In this design metering is entirely controlled by the output capillary pipette according to an embodiment of the invention.

Metering by the volume of the pooling channel under the PSM can still be achieved if the speed of filling of the output capillary tube, or other output structure, exceeds the speed of lateral flow of the plasma to fill, or re-fill, the pooling channel. But, in the case of an automatic, stand-alone centrifuge replacement device, with an output capillary pipette, it is better for the output capillary to control metering due to the three benefits described above with reference to FIG. 4. An example of a device using these three benefits is illustrated in FIG. 7, where the normal metering plasma pooling channel 410 of earlier figures is replaced with a shorter, deeper and non-metering plasma pooling channel 413, and the venting duct 330 of previous figures is no longer used.

CPR-Valve Double Duty: Despite the three benefits described above, the desired processing and collection volume of plasma may be far larger than can be accommodated using thicker adhesives, shorter pooling channels or other means of balancing the capillary force equations discussed previously. According to equation (7), and using the same materials and geometries mentioned in that case, if the output capillary has a radius that is larger than 3.7 times the effective hydraulic radius of the plasma pooling channel, then the interface between the output capillary and the plasma pooling channel represents a capillary stop junction and the plasma will not enter into the output capillary.

However, the whole point of this disclosure and function of the CPR-Valve or mechanism, is to not be limited by capillary stop junctions or other capillary barriers that may exist in certain systems. As is illustrated in FIG. 8, the CPR-Valve 200 can be designed to serve a dual purpose, both to eliminate the breakthrough pressure of the PSM 100, and to simultaneously overcome the capillary stop junction present at the inlet of the output capillary 600.

Figure 8:
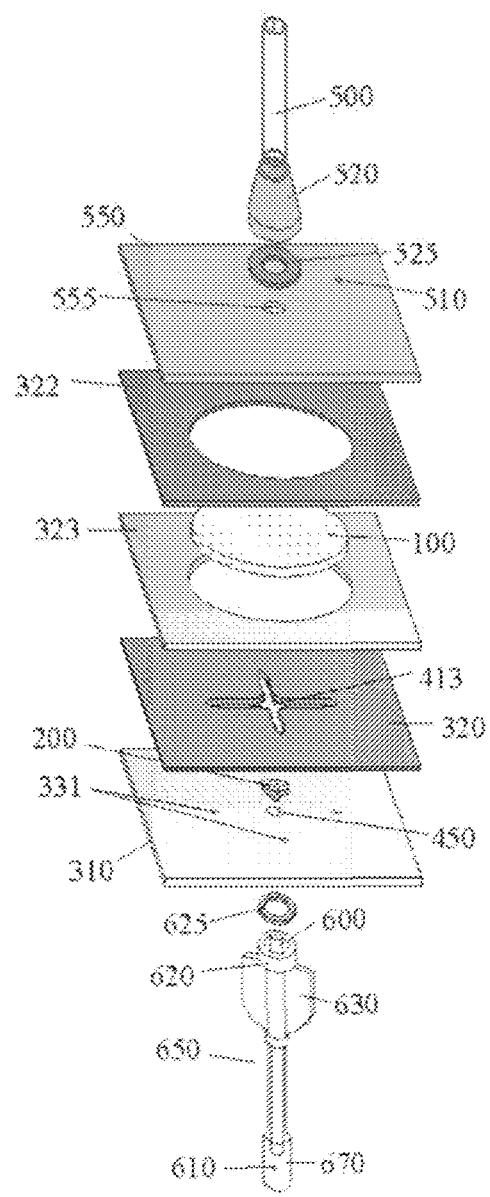
FIG. 8 illustrates a design where the CPR-Valve serves a dual purpose, namely to draw plasma through the PSM and to overcome the capillary stop junction at the entrance of the large inner-diameter capillary pipette by drawing plasma into the capillary pipette, according to an embodiment of the invention.
Figure 9:
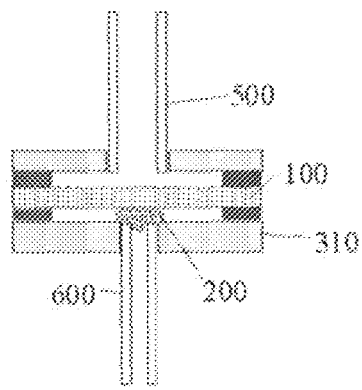
FIG. 9 illustrates further a profile view of the CPR-Valve and its placement between the PSM and output capillary pipette in order to perform the dual purpose mentioned in connection with FIG. 8, according to an embodiment of the invention.

Both the illustration in FIG. 8, and further detail shown in FIG. 9, the CPR-Valve 200 is placed between the output capillary 600 and the PSM 100, with a portion of the CPR-Valve extending past the output capillary 600 to lie between the PSM 100 and base 310. The CPR-Valve first overcomes the breakthrough pressure of the PSM, causes the meniscus of the pooling plasma to spread radially outward through the channels, spokes or arms of the plasma pooling area 413 extending from the center and reaching out to the edges of the PSM, and at the same time introduces the plasma into the output capillary. As in the short channel design illustrated in FIG. 7, this design relies on plasma flowing laterally in the PSM before it empties into the collection channels. The number of spokes or channels can be optimized depending on the desired speed of collection, surface area of the PSM, device fabrication, assembly and reliability issues.

Timing of the spreading plasma and its introduction into the output capillary is important. If the thickness of the adhesive 320, or channel depth between the PSM 100 and base 310, is kept very small or thin such as between 25-50 μm, and the width of each channel 413 is kept small, such as less than 1 mm, the meniscus will spread outward rapidly. Although a larger number of branches or spokes could increase the speed of filling the output capillary, it also increases the chance of one branch not filling properly and trapping a bubble instead. If the CPR-Valve 200 introducing plasma into the output capillary 600 is slightly thicker, or denser than it is outside the capillary where it contributes to overcoming the PSM breakthrough pressure, then it will take a slightly longer time for the plasma to be introduced into the output capillary 600. It is important that sufficient plasma has passed into the pooling space or branches 413 and extends to the pooling area vents 331, before the plasma is drawn into the output capillary 600, so the output capillary does not draw an air bubble into it rather than plasma. In this case the vents 331 shown in FIG. 8 are not used to introduce air into the pooling area as plasma enters the output capillary, as is the case for vents 330 shown in previous figures, but rather to vent air out of the pooling channels 413 as they fill, beginning at the center of the device where the CPR-Valve 200 is located, and expanding radially outward. If plasma reaches the vents 331, air will not re-enter through the vent into the pooling channels 413 because the adhesive layer 320 is so thin, a strong capillary junction exists at the point of the vent 331, and air will not enter. In this case, the total volume of plasma in the pooling channels 413 will contribute to the dead volume of the system because it cannot be collected into the output capillary.

Initially plasma is drawn into the output capillary by capillary force. But, depending on the geometry and volume of the output capillary, at some point the weight of the liquid column (if the device is held upright) will begin to act as a suction source that will draw an air bubble into the capillary 600 if plasma in the channels 413 have not yet reached the output vents 331. This appears to become a factor when the liquid column height in the output capillary 600 approaches 20 mm or greater. To prevent this from happening, the pooling space or channels under the PSM should be filled with plasma rapidly without trapping bubbles. Alternatively, the device could be placed on its side to minimize any suction pressure that is generated by the column of plasma in the output capillary. In this case the squeeze bulb 670 should be resting on the support surface, such as a table, with the inlet of the capillary, within the device, slightly higher in elevation than the squeeze bulb. This will allow capillary forces to continue to function properly and gravitation forces to only be slightly additive, but weaker than if the device is in a vertical position.

In the case where the CPR-Valve 200 is between the output capillary 600 and the PSM 100, if the soluble material comprising the CPR-Valve is dyed, it can be observed that the material is first drawn radially outward by the radially expanding meniscus, but then is it drawn inward by the flow of plasma entering the output capillary. In contrast to the previous design where most or all of the CPR-Valve material can be excluded from the collected plasma volume, in the current design FIGS. 8 and 9 the CPR-Valve material, either entirely or in large part, will be drawn into the output capillary rather than cut-off from collection, as has been described previously. In this case it is of more importance for the material comprising the CPR-Valve to not be an interferent in any downstream process, such as in biomarker detection, than in the case when all or the majority of dissolved CPR material is excluded from collection.

Figure 10:
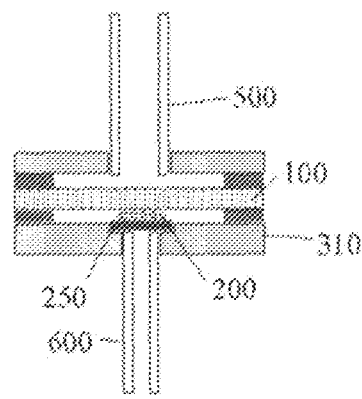
FIG. 10 illustrates a profile view of the CPR-Valve and its placement between the PSM and a reagent pellet or disk and the output capillary pipette according to an embodiment of the invention.

Integrated Reagent: As has been mentioned, in the design illustrated in FIGS. 8 and 9, all or the majority of the material comprising the CPR-Valve 200 will be collected by the output capillary 600. Thus, the material should not interfere in downstream processes, and since it is reliably and repeatedly passed downstream, the CPR-Valve can be comprised of materials important to downstream processing. This is illustrated in FIG. 10 where a reagent disk 250 is located between the CPR-Valve 200 and the output capillary 600.

Instead of being 2 different structures or materials, the CPR-Valve 200 and reagent disk 250 can also be the same structure and material, depending on the needs of the system. In this case the plasma separation device is not necessarily an independent stand-alone centrifuge replacement tool but, due to the presence of a specific reagent that is closely associated with a specific application or diagnostic test where the reagent is used, it becomes an integral component of a specific diagnostic application or test. The reagent 250 should also be present in excess of the minimum needs of the application, to ensure adequate reagent is present in the downstream system if not all of the reagent is collected in the output capillary 600. A common example of this is conjugate reagent being present in excess for downstream lateral flow devices.

In many diagnostic applications reagents are present in the form of lyophilized beads or pellets. It is possible they can be in the form of a disk that is in contact with the CPR-Valve 200. It is also possible the reagent can be used as a CPR-Valve. The primary requirements of a CPR-Valve are that is possesses high capillarity in dry form, to draw liquid out of the PSM, that it facilitates the generation of a meniscus between the PSM and base of the device, and that it is readily soluble in the filtrate or plasma without increasing the filtrate or plasma's viscosity to any great degree. Some characteristics of lyophilized materials may not allow it to be used as a CPR-Valve, and may complicate the introduction of liquid into the output capillary, such as very rapid if not explosive dissolution or disintegration in the presence of liquid, which may complicate meniscus formation or inject bubbles into the output capillary. If this is the case the reagent 250 could be placed near the CPR-Valve 200 and/or output capillary 600, rather than used instead of the CPR-Valve or in contact with the output capillary. Even in this condition it is very likely the majority of the reagent will be collected into the output capillary during the separation and collection process.

Surface Area, Hematocrit and Input and Output Volumes: Because most PSMs are asymmetric size exclusion filters, ranging from large pore size at the top to smaller pore size at the bottom, if sufficient blood is passed through them, they will eventually clog with cells preventing further plasma separation or extraction. Because of this, commercial PSMs are often rated in volume of input blood per square centimeter of surface area of the filter, or membrane.

For example, the GR grade of the Pall Vivid PSM states 40-50 µL of whole blood input per square centimeter of membrane surface area. However, in the laminated designs illustrated in FIGS. 2, 4-8, a large portion of the bottom surface of the PSM is blocked by adhesive 320, which is used to support the membrane and to define the geometry of the plasma pooling area 410, 411, 412 or 413. Unfortunately, however, this does not mean that the corresponding upper surface of the PSM does not need to be covered, which would reduce the total volume of whole blood required. Experimental analysis has shown that the entire upper surface area and total depth of the PSM must be saturated with the input whole blood in order for the devices to function properly. This reduces the efficiency of separation. In a thermoformed or injection molded design, however, it is possible to pinch or squeeze-off a portion of the upper surface area and corresponding depth or thickness of the PSM, which would allow an upper surface area to approximately equal the top of the plasma pooling area. This would increase the efficiency of the system.

Another factor effecting potential plasma volume is the hematocrit of the input whole blood sample. Hematocrit is the ratio of whole blood volume to packed cellular components of the blood. A low hematocrit represents a low cellular component of blood and larger liquid, or plasma component. A high hematocrit represents a higher cellular component and lower liquid or plasma component. Typical physiological ranges of hematocrit variability among healthy individuals is between 38-55%, meaning a maximum volume of 62 µL of plasma could be extracted from an individual with a hematocrit of 38%, if the starting whole blood volume were 100 µL, but only 50 µL if their hematocrit were 50%. In addition, unhealthy individuals, or people acclimated to extreme conditions, such as high altitude, infants, and other sub-groups may have hematocrit ranges much broader than this. Hematocrit variability, if not accounted for, can represent a significant variation and source of error in blood-based diagnostics, where the measurement of biomarkers and their physiological significance is measured in units of plasma or serum and not whole blood.

In order to ensure proper device function, and taking into account dead volume, surface area specifications, blood or plasma retained with the PSM or overall efficiency in separation of the PSM, and potential hematocrit variability, a device that specifies a fixed and accurate plasma extraction, metering and dispensing capability will, by its nature, be inefficient in its ability to collect the total volume of plasma available in a sample.

Depending on the overall design of the devices illustrated in the figures, and depending on whether they are molded, thermoformed or laminated, and depending on the allowable range of hematocrit that can be accommodated for, the devices disclosed in this filing are capable of extracting approximately 1 µL of plasma from every 3 to 6 µL of whole blood input.

Another embodiment of the technology is illustrated in FIG. 11, where the efficiency of the system can be improved by having an extension 415 of the plasma pooling area 410 that extends past the boundary of the PSM 100. The depth or thickness of the pooling area cannot be too thick because of the difficulty in establishing a meniscus between the upper and lower surfaces, and because of the need for capillary forces to help drive the meniscus, which capillary forces may become too weak if the thickness or depth of the pooling area 410 becomes too large, such as greater than 300 µm. However, a microchannel or extension 415 with a higher capillary force than the pooling area 410 directly under the PSM 100 can serve to draw some of the plasma out from under the PSM, which is replaced by more plasma passing through the PSM. The interface to the output capillary 600 could then connect with this extension 415. However, in this case the capillarity of the output capillary 600 must be higher than the capillarity of the extension 415, rather than the capillarity of the pooling area 410 under the PSM 100.

Input Volume Metering: As has been mentioned, depending on a capillary tube's geometry (e.g., inner-diameter) and composition (e.g., glass or plastic), and the liquid that it holds (e.g., blood) which define its capillarity, gravity can have an effect on the position or movement of liquid inside. For example, a small amount of plasma can extend past the end of the output capillary, signaling it is full. This is due to the weight of the liquid pushing on the meniscus, and the fact that it the rim and edges of the capillary may still have strong capillary forces, or high surface energy, allowing the plasma to migrate slowly down and out when, theoretically, the abrupt end of the capillary should represent a stop junction which should prevent any further movement of the plasma. This creeping outward is slowed or stopped when the capillary is held in a horizontal position, indicating gravity has an effect on the liquid in the capillary.

Factors that influence the spread of liquid out of the capillary include the height of the column of liquid, the ID (inner-diameter) of the capillary, its density which, together with ID and column height indicate the mass of the liquid, the thickness of the glass capillary walls and the angle of the capillary with respect to gravity.

For example, it has been observed that, when held vertically, the blood within a 1 mm ID glass hematocrit tube will extend past the bottom of the tube by about 1 mm if the column of blood within the tube is at least 30 mm in height. But, it will only extend past the bottom of the tube by about 0.5 mm if the column height is reduced to about 25 mm. Also, the edges of the extension of the meniscus past the end of the tube can be seen to migrate from being constrained to the inner walls of the capillary to move to the outer edge of the capillary when the column is higher.

If a first capillary tube, where the sample is introduced, is held in a slightly inclined position such that the distal end is slightly elevated above the proximal end, between 0.5 to 30 degrees up from the horizontal, the sample should fill the tube automatically by capillary force and stop at the distal end. If the distal end is enclosed in another capillary tube that has an ID (inner-diameter) that tightly fits with the OD (outer diameter) of the first tube, the capillary stop junction at the distal end of the first tube should still stop the flow of liquid filling it at its proximal end. Even though it is enclosed in a second tube, the ID of the flow channel still increases sufficiently to generate a capillary stop junction.

If, however, once the first tube fills to its end point, both tubes are held upright or vertical, depending on the length of the first tube, the weight of liquid inside it can be sufficient to draw it past its stop junction until the extended meniscus contacts the ID of the second tube, causing it to move forward, eliminating the stop junction, and allowing liquid to move forward. In this case the weight of the liquid in the column breaks the capillary stop junctions at both the inlet and outlet of the first capillary tube.

This situation is illustrated in FIGS. 12 a and b where the distal capillary stop junction 580 of the first capillary tube 500 can be used to precisely meter the input volume of liquid (blood) 900 that is loaded into the first tube as it is in its loading position, with the distal end slightly elevated above the input. However, when the system is held upright the weight of the sample 900 can push it past this stop junction 580 and into the second tube 590, which leads to the downstream device which must have appropriate properties to draw in the metered input volume, such as by having sufficient capillarity to draw liquid out of the first 500 and second 590 capillary tubes, in this case a PSM 100.

This design can more precisely meter the input of a system where more precise metering is important. In the design mentioned previously only a minimum volume of input is ensured, but the maximum was not controlled. In this new design the minimum and maximum are controlled, by filling to the stop junction 580 of the first capillary 500, which can be visibly observed. An example of when input metering is more critical is when the plasma extraction device disclosed herein is optimized for function as a hematocrit measurement device, where both input and output are measured.

Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A device for collecting a metered volume of liquid from a liquid filtrate sample, the device comprising:
at least one filtration membrane;
at least one filtrate collection structure to collect liquid drawn through the filtration membrane, the liquid drawn through the filtration membrane constituting the liquid filtrate sample;
at least one liquid collection structure enclosing a known volume and possessing sufficient capillarity to fill with and thereby meter a volume of liquid drawn from the liquid filtrate sample in the filtrate collection structure, the liquid collection structure comprising a capillary tube and a fitting, the capillary tube being removably attached to the filtrate collection structure via the fitting; and
an indicator region at a distal end of the liquid collection structure, the indicator region configured to visibly indicate when the capillary tube has filled with the liquid drawn from the liquid filtrate sample.

2. The device of claim 1, wherein the indicator region comprises a soluble colored dye or contrasting agent deposited on an inside surface of the capillary tube, wherein the dye or contrasting agent dissolves in the liquid drawn from the liquid filtrate sample once said liquid fills the capillary tube.

3. The device of claim 1, wherein the indicator region comprises one or more scratches or marks on an inside surface of the capillary tube, wherein the scratches or marks visually disappear once the liquid drawn from the liquid filtrate sample fills the capillary tube.

4. The device of claim 1, wherein the indicator region comprises a hydrophobic film on an inside surface of a distal portion of the capillary tube that prevents the distal portion of the capillary tube from filling with the liquid drawn from the liquid filtrate sample, thereby providing a visible contrast between filled and unfilled portions of the capillary tube once the liquid drawn from the liquid filtrate sample fills the capillary tube up to and excluding the distal portion.

5. The device of claim 1, wherein the liquid collection structure comprises a squeeze bulb for dispensing the metered volume of liquid drawn from the liquid filtrate sample following removal of the capillary tube from the filtrate collection structure.

6. The device of claim 5, wherein the squeeze bulb comprises a vent.

7. The device of claim 5, wherein the liquid collection structure comprises a plastic sheath surrounding the capillary tube, the plastic sheath defining finger gripping points on the capillary tube.

8. The device of claim 1, wherein the at least one filtration membrane comprises a plasma separation membrane.

9. The device of claim 1, wherein the filtrate collection structure comprises a base material and walls that, together with the at least one filtration membrane, enclose a filtrate pooling space.

10. The device of claim 1, wherein the at least one filtrate collection structure comprises a base material and walls that, together with the at least one filtration membrane, enclose first and second filtrate pooling spaces, and wherein the at least one liquid collection structure comprises a first liquid collection structure configured to fill with and meter a first volume of liquid drawn from the first filtrate pooling space and a second liquid collection structure configured to fill with and meter a second volume of liquid drawn from the second filtrate pooling space.

11. The device of claim 1, further comprising an input metering capillary configured to deliver a minimum volume of liquid sample to an upstream surface of the at least one filtration membrane.

12. The device of claim 11, further comprising a cover or cap associated with the input metering capillary that is put on the input metering capillary once the liquid collection structure has filled with the liquid drawn from the liquid filtrate sample.

13. A device for collecting a metered volume of liquid from a liquid filtrate sample, the device comprising:
at least one filtration membrane;
an input metering capillary configured to deliver a minimum volume of liquid sample to an upstream surface of the at least one filtration membrane,
at least one filtrate collection structure to collect liquid drawn through the filtration membrane, the liquid drawn through the filtration membrane constituting the liquid filtrate sample;
at least one liquid collection structure enclosing a known volume and possessing sufficient capillarity to fill with and thereby meter a volume of liquid drawn from the liquid filtrate sample in the filtrate collection structure;
an indicator region at a distal end of the liquid collection structure, the indicator region configured to visibly indicate when the liquid collection structure has filled with the liquid drawn from the liquid filtrate sample; and a cover or cap associated with the input metering capillary that is put on the input metering capillary once the liquid collection structure has filled with the liquid drawn from the liquid filtrate sample.

14. The device of claim 13, wherein the indicator region comprises a soluble colored dye or contrasting agent deposited on an inside surface of the liquid collection structure, wherein the dye or contrasting agent dissolves in the liquid drawn from the liquid filtrate sample once said liquid fills the liquid collection structure.

15. The device of claim 13, wherein the indicator region comprises one or more scratches or marks on an inside surface of the liquid collection structure, wherein the scratches or marks visually disappear once the liquid drawn from the liquid filtrate sample fills the liquid collection structure.

16. The device of claim 13, wherein the indicator region comprises a hydrophobic film on an inside surface of a distal portion of the liquid collection structure that prevents the distal portion of the liquid collection structure from filling with the liquid drawn from the liquid filtrate sample, thereby providing a visible contrast between filled and unfilled portions of the liquid collection structure once the liquid drawn from the liquid filtrate sample fills the liquid collection structure up to and excluding the distal portion.

17. The device of claim 13, wherein the liquid collection structure comprising a capillary tube and a squeeze bulb for dispensing the metered volume of liquid drawn from the liquid filtrate sample following removal of the capillary tube from the filtrate collection structure.

18. The device of claim 13, wherein the at least one filtration membrane comprises a plasma separation membrane.

19. The device of claim 13, wherein the filtrate collection structure comprises a base material and walls that, together with the at least one filtration membrane, enclose a filtrate pooling space.

20. The device of claim 13, wherein the at least one filtrate collection structure comprises a base material and walls that, together with the at least one filtration membrane, enclose first and second filtrate pooling spaces, and wherein the at least one liquid collection structure comprises a first liquid collection structure configured to fill with and meter a first volume of liquid drawn from the first filtrate pooling space and a second liquid collection structure configured to fill with and meter a second volume of liquid drawn from the second filtrate pooling space.

* * * * *